United States Patent [19]

Katsumata et al.

[11] Patent Number: 5,595,894
[45] Date of Patent: Jan. 21, 1997

[54] PROCESS FOR STABLY MAINTAINING RECOMBINANT PLASMIDS IN SERINE AUXOTROPHIC MICROORGANISMS BELONGING TO THE GENUS CORYNEBACTERIUM OR BREVIBACTERIUM

[75] Inventors: Ryoichi Katsumata, Machida; Masato Ikeda, Sagamihara; Keiko Nakanishi, Machida; Yuko Sasao, Tokyo, all of Japan

[73] Assignee: Kyowa Hakko Kogyo Co. Ltd., Japan

[21] Appl. No.: 439,803

[22] Filed: May 12, 1995

Related U.S. Application Data

[62] Division of Ser. No. 354,314, Dec. 12, 1994, which is a continuation of Ser. No. 795,917, Nov. 20, 1991, abandoned.

[30] Foreign Application Priority Data

Nov. 22, 1990 [JP] Japan ................................ 2-320440

[51] Int. Cl.⁶ .......................... C12N 15/09; C12N 1/20; C12P 13/04
[52] U.S. Cl. ................... 435/172.1; 435/252.32; 435/106; 435/840; 435/843
[58] Field of Search ................ 435/69.1, 172.1, 435/320.1, 106, 252.32, 840, 843; 935/56

[56] References Cited

U.S. PATENT DOCUMENTS

| | | | |
|---|---|---|---|
| 4,489,160 | 12/1984 | Katsumata et al. | 435/91.4 |
| 4,500,640 | 2/1985 | Katsumata et al. | 435/252.32 |
| 4,617,267 | 10/1986 | Katsumata et al. | 435/91.4 |
| 4,681,847 | 7/1987 | Katsumata et al. | 435/172.3 |
| 4,683,205 | 7/1987 | Katsumata et al. | 435/172.3 |
| 4,710,471 | 12/1987 | Katsumata et al. | 435/252.32 |
| 4,775,623 | 10/1988 | Katsumata et al. | 435/114 |
| 4,874,698 | 10/1989 | Ozaki et al. | 435/108 |
| 4,908,312 | 3/1990 | Ozaki et al. | 435/108 |
| 4,927,758 | 5/1990 | Mizukami et al. | 435/107 |
| 4,954,441 | 9/1990 | Katsumata et al. | 435/115 |
| 5,017,482 | 5/1991 | Katsumata et al. | 435/114 |
| 5,407,824 | 4/1995 | Katsumata et al. | 435/232.32 |

FOREIGN PATENT DOCUMENTS

| | | |
|---|---|---|
| 87/76589 | 2/1988 | Australia . |
| 263515 | 4/1986 | European Pat. Off. . |
| 204326 | 12/1986 | European Pat. Off. . |
| 219027 | 4/1987 | European Pat. Off. . |
| 0219022 | 4/1987 | European Pat. Off. . |
| 233581 | 8/1987 | European Pat. Off. . |
| 0219027 | 9/1987 | European Pat. Off. . |
| 259858 | 3/1988 | European Pat. Off. . |
| 264914 | 4/1988 | European Pat. Off. . |
| 338474 | 10/1989 | European Pat. Off. . |
| 0352763A1 | 1/1990 | European Pat. Off. . |
| 352763A1 | 1/1990 | European Pat. Off. . |
| 0401735A1 | 12/1990 | European Pat. Off. . |
| 91310709 | 12/1992 | European Pat. Off. . |
| 63-119688A | 5/1988 | Japan . |
| 63-102692 | 7/1988 | Japan . |
| 0901735 | 11/1970 | WIPO . |
| PCT/US88/03496 | 10/1988 | WIPO . |
| 0401735 | 12/1990 | WIPO . |

OTHER PUBLICATIONS

Skogman et al., Gene, 23:105–115, 1983.
Nilsson and Skogman, Bio/Technology, 4:901–903, 1986.
Ferrari et al., Bio/Technology, 3:1003–1007.
Ozaki et al., Mol. Gen. Genet., 196:175–178, 1984.
Saito and Miura, Biochim. Biophys. Acta, 72:619–629, 1963.
Sugimoto and Pizer, J. Biol. Chem., 243(9):2081–2089, 1968.
Follettie and Sinskey, Food Technology, 1986, "Overview: Outstanding Symposia in Food Science & Technology: Application of Genetic Engineering to Fermentation", Oct., No. 10, pp. 88–94.
Tobey et al., J. Biol. Chem. 261(26):12179–12183 (1986).

*Primary Examiner*—George C. Elliott
*Assistant Examiner*—Thanda Wai
*Attorney, Agent, or Firm*—Pennie & Edmonds

[57] ABSTRACT

The present invention provides a process for producing substances such as L-tryptophan and L-threonine, which comprises transforming a serine-requiring microorganism belonging to the genus Corynebacterium or Brevibacterium by incorporation of a recombinant plasmid containing a gene which complements the serine-requirement of the host and a gene which relates to the biosynthesis of a desired substance; culturing the obtained transformant in a culture medium; allowing the substance produced by the transformant to accumulate in the culture; and recovering the substance from the culture.

3 Claims, 2 Drawing Sheets

PROCESS FOR STABLY MAINTAINING RECOMBINANT PLASMIDS IN SERINE AUXOTROPHIC MICROORGANISMS BELONGING TO THE GENUS CORYNEBACTERIUM OR BREVIBACTERIUM

This is a division of application Ser. No. 08/354,314, filed Dec. 12, 1994 which is a file wrapper continuation of application Ser. No. 07/795,917 filed Nov. 20, 1991, currently abandoned.

FIELD OF THE INVENTION

The present invention relates to a process for producing substances using a microorganism belonging to the genus Corynebacterium or Brevibacterium and carrying a recombinant plasmid. Microorganisms belonging to the genus Corynebacterium or Brevibacterium are widely utilized to produce various amino acids by fermentation.

BACKGROUND OF THE INVENTION

Improvement of microorganisms of the genus Corynebacterium or Brevibacterium by recombinant DNA technology has been attempted using host-vector systems for these genera. However, recombinant plasmids introduced into a host microorganism are often unstable and are liable to be lost from the host. Therefore, the instability of a recombinant plasmid is one of the serious problems to be solved for practical use of the microorganisms constructed by recombinant DNA technology in an industrial process for producing amino acids.

So far, several methods to stabilize plasmids in host cells have been reported in microorganisms of genera other than Corynebacterium and Brevibacterium. These methods are classified into two types according to the manner of stabilization. First, genetic stabilization of a plasmid is known. For example, as for *Escherichia coli*, it is known that the par gene which relates to stable distribution of the low copy number plasmid pSC101 is inserted into the plasmid [Gene, 23, 105 (1983)]. Likewise, as for strains of the genus Corynebacterium or Brevibacterium, it is known stabilize a plasmid capable of autonomous replication in Coryneform bacteria of the genus Brevibacterium in such bacteria by insertion of a gene which is present on a plasmid carried by *Brevibacterium stationis* (EP-352763A1). Such methods afford improvement in stability of a plasmid to some extent, but are not suitable for an industrial process for amino acid production involving several-steps of seed culturing because it is known that plasmids are liable to be lost from host cells through repetitions of cell division for proliferation during cultivation [Bio/Technology, 4, 901 (1986)]. Second, methods for selectively growing plasmid-carrying cells by inhibiting the growth of cells from which a plasmid has been lost are known. For example, in small scale cultivation, antibiotics are usually added to the culture medium. However, such addition of antibiotics is costly in large scale cultivation. Further, the purification step for removal of the added antibiotics is required, and thus this method is not suitable for an industrial process. As a method without such addition of specific substances, it is known to stabilize plasmid in host cells by using a combination of a host strain which has deficiency in a gene essential for its growth and a plasmid containing a gene which complements the deficiency. For example, for *Bacillus subtilis*, a combination of a host strain which is deficient in the alanine racemase gene and a plasmid containing the alanine racemase gene of which type is employed [Bio/Technology, 3, 1003 (1985)]; and for *Escherichia coli*, a combination of a diaminopimelic acid-requiring host strain and a plasmid containing a gene which complements the requirement is employed (Japanese Published Unexamined Patent Application No. 233790/88). In both cases, plasmid-free cells are lysed because of their incapability of synthesizing D-alanine or diaminopimelic acid which is essential component of their cell walls, and thus only cells carrying the plasmids can grow normally. These methods are applicable to a cultivation processes using culture media which contain extracts derived from animals, plants or yeasts and which are usually used in industrial fermentation processes, as such natural nutrients do not contain D-alanine or diaminopimelic acid.

However, it is difficult to apply these methods to microorganisms which have isozymes of alanine racemase or have a bypass of diaminopimelic acid biosynthetic pathway because D-alanine or diaminopimelic acid-requiring mutants of such microorganisms can not be readily obtained.

In the large scale industrial production of substances such as amino acids by using strains of the genus Corynebacterium or Brevibacterium carrying recombinant plasmids, cells proliferate by repetitions of division through steps from seed culture to fermentation for the production, during which the recombinant plasmids are often lost from the cells. This instability of the plasmids causes a reduction of productivity, and therefore, it is desired to develop a method to stabilize recombinant plasmids in the host cells, leading to the industrial production of substances at low cost.

There is no report on the stabilization of a plasmid in a host strain by the use of a mutant having requirement for substances contained in natural nutrients added as medium components, e.g. amino acids, as the host, and a plasmid containing a gene which complements the requirement of the host as the vector. Such a combination has been considered to be inappropriate as a host-vector system for stabilizing a plasmid in a host strain because cells from which plasmids have been lost can also grow.

SUMMARY OF THE INVENTION

The present invention provides a process for producing substances such as L-tryptophan and L-threonine, which comprises transforming a serine-requiring microorganism belonging to the genus Corynebacterium or Brevibacterium by incorporation of a recombinant plasmid containing a gene which complements the serine-requirement of the host and a gene which relates to the biosynthesis of a desired substance; culturing the obtained transformant in a culture medium; allowing the substance produced by the transformant to accumulate in the culture; and recovering the substance from the culture.

Figure 1:
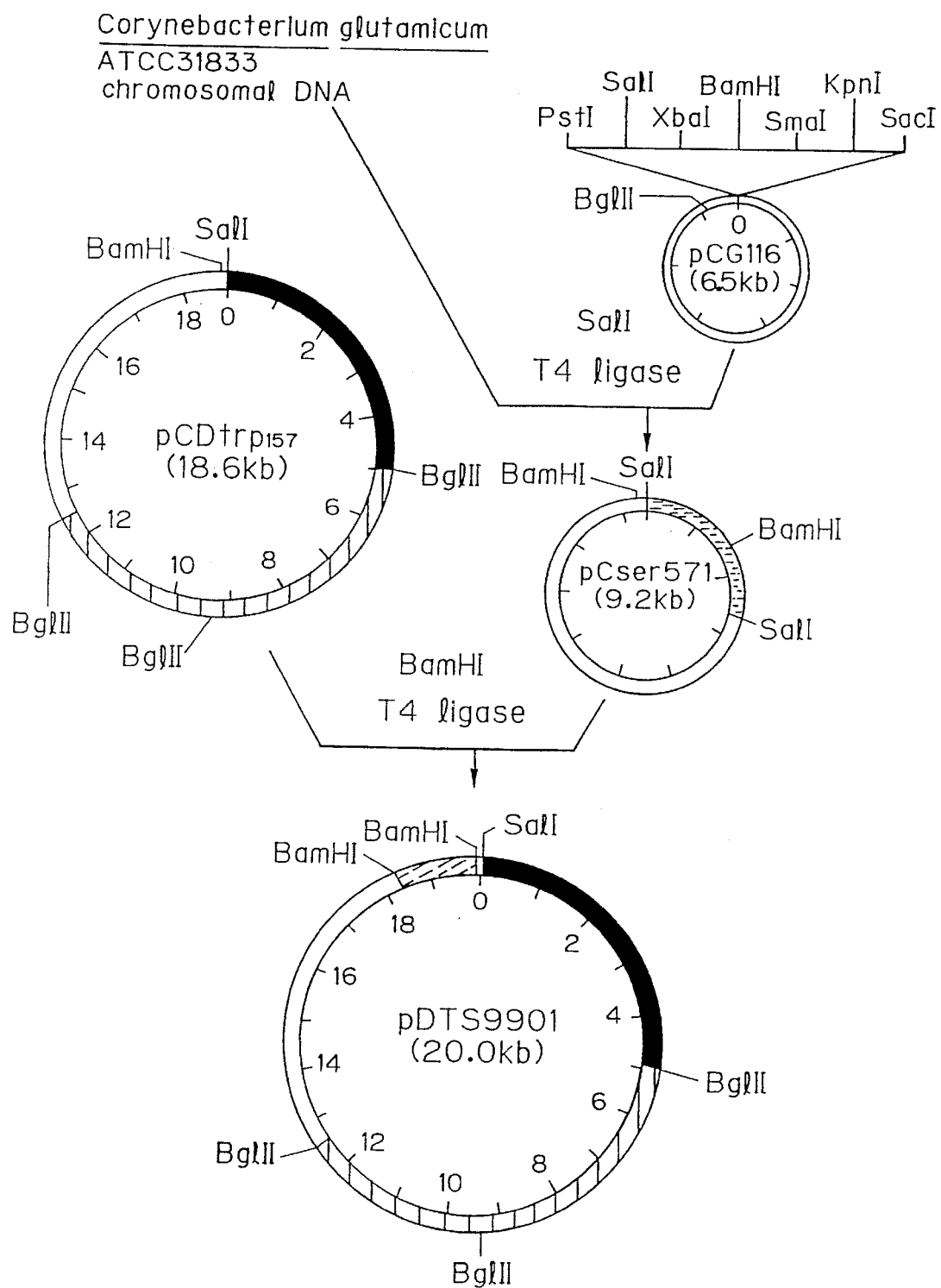
FIG. 1 illustrates the restriction enzyme cleavage map for pDTS9901 and the steps for constructing it. The 3-deoxy-D-arabino-heptulosonate-7-phosphate synthase (DS) gene is located on the chromosomal DNA fragment indicated by a thick solid line, the tryptophan biosynthetic gene cluster is located on the chromosomal DNA fragment indicated by slant lines, and the 3-phosphoglycerate dehydrogenase (PGDH) gene is located on the chromosomal DNA fragment indicated by broken lines.

The sizes of plasmids are indicated by kilobase (kb).

DETAILED DESCRIPTION OF THE INVENTION

As microorganisms belonging to the genus Corynebacterium or Brevibacterium are capable of rapidly metabolizing serine, serine which is contained in a culture medium is rapidly metabolized at the early stage of their growth. Consequently, serine-requiring host cells from which the plasmid has been lost cannot grow and only plasmid-carrying cells can be subjected to subculture. This results in efficient production of the substances compared with conventional processes using transformants.

In the present invention, any serine-requiring strain belonging to the genus Corynebacterium or Brevibacterium can be used as the host microorganism. These serine requiring strains may have other properties such as requirement for various nutrients and resistance or sensitivity to chemicals. Theses trains may be derived from the following strains.

| | |
|---|---|
| Corynebacterium glutamicum | ATCC 13032 |
| Corynebacterium acetoacidophilum | ATCC 13870 |
| Corynebacterium herculis | ATCC 13868 |
| Corynebacterium lilium | ATCC 15990 |
| Brevibacterium flavum | ATCC 14067 |
| Brevibacterium lactofermentum | ATCC 13869 |
| Brevibacterium divaricatum | ATCC 14020 |
| Brevibacterium thiogenitalis | ATCC 19240 |

The serine-requiring mutants used in the present invention can be obtained by subjecting the parent strains to ordinary treatments of mutagenesis, for example, ultraviolet irradiation and chemical treatment with N-methyl-N'-nitro-N-nitrosoguanidine (NTG) or nitrous acid, and then selecting mutants which can not grow on a minimal medium but can grow on a minimal medium containing serine.

The gene which complements the serine-requirement of a host strain may be derived from any microorganism. When the host is a mutant which has deficiency in the gene encoding an enzyme in the serine biosynthetic pathway, genes relating to the biosynthesis of serine such as the 3-phosphoglycerate dehydrogenase gene, the phosphoserine aminotransferase gene and the phosphoserine phosphatase gene may be used.

As the vector for inserting the DNA, any vector which is capable of autonomous replication in glutamic acid-producing Coryneform bacteria may be used. For example, plasmids such as pCG1 (Japanese Published Unexamined Patent Application No. 134500/821, pCG2 ( Japanese Published Unexamined Patent Application No. 35197/83), pCG4 and pCG11 (Japanese Published Unexamined Patent Application No. 183799/82), pCE54 and pCB101 (Japanese Published Unexamined Patent Application No. 105999/83), and pCE51, pCE52 and pCE53 [Mol. Gen. Genet., 196, 175 (1984)] can be used.

The gene which complements the serine-requirement of the host strain can be obtained in the following manner. That is, the above-mentioned serine-auxotrophic host strain is transformed with a mixture of recombinant DNAs obtained by recombination of the chromosomal DNA and the vector DNA, and the recombinant DNA containing the said gene is isolated from a serine-non-requiring transformant. Transformation can be carried out by the method using protoplasts (Japanese Published Unexamined Patent Applications Nos. 186492/82 and 186489/82).

The serine-requiring mutant and recombinant plasmid containing the gene which complements the serine requirement of the host obtained as above is used as the host-vector system for having a DNA fragment containing a desired gene stably maintained in a microorganism of the genus Corynebacterium or Brevibacterium. Alternatively, a recombinant plasmid which contains a DNA fragment containing a desired gene may be constructed by using another host-vector system and then used for constructing a recombinant plasmid further containing the gene which complements the serine-requirement of the host. The obtained recombinant plasmid is introduced into the serine-requiring mutant to be stably maintained.

The term desired gene means a gene which confers the productivity of a desired substance on a microorganism of the genus Corynebacterium or Brevibacterium or improve the production yield of the substance in such a microorganism when introduced therein. Suitable examples are genes encoding enzymes which catalyze rate-limiting reactions in the biosynthetic pathways of amino acids (Japanese-Published Unexamined Patent Applications Nos. 265892/89, 105688/88, 156292/84, 24192/85, 34197/85, 94985/88, 156294/84, 30693/85, 91193/87, 209597/86, 66989/85, 79597/88, 102692/88, 119688/88, 79788/87, 186795/87 and 68091/88).

Cultivation of the transformant obtained by introducing the recombinant plasmid containing the gene which complements the serine-requirement of the host and the desired gene into the serine-requiring microorganism may be carried out using a medium containing carbon sources, nitrogen sources, inorganic substances, amino acids, vitamins, etc. at a controlled temperature and pH under aerobic conditions.

As the carbon sources, carbohydrates such as glucose, glycerol, fructose, sucrose, maltose, mannose, starch, starch hydrolyzate, and molasses; polyalcohols; and various organic acids such as pyruvic acid, fumaric acid, lactic acid, and acetic acid may be used. Blackstrap molasses is especially suitable. Depending upon the assimilability of strain employed, hydrocarbons and alcohols may also be used.

As the nitrogen sources, ammonia; various inorganic and organic ammonium salts such as ammonium chloride, ammonium sulfate, ammonium carbonate, and ammonium acetate; urea and other nitrogen-containing substances; and nitrogen-containing organic substances such as peptone, NZ-amine, meat extract, yeast extract, corn steep liquor, casein hydrolyzate, fish meal and digested products thereof, and chrysalis hydrolyzates may be used.

As the inorganic substances, dipotassium hydrogen phosphate, potassium dihydrogen phosphate, ammonium sulfate, ammonium chloride, magnesium sulfate, sodium chloride, ferrous sulfate, manganese sulfate, and calcium carbonate, etc. may be used. Depending upon the carbon source or nitrogen source of a culture medium, amino acids and vitamins such as biotin and thiamine may be added to the culture medium if desired. Additionally, if the strain requires a specific substance for growth, it is necessary to add to such substance to the culture medium. Cultivation is carried out under aerobic conditions, for example, by shaking the culture or by aeration-stirring of the culture, preferably at a temperature in the range of 20°–40° C. The pH of the culture medium is preferably maintained around neutral during the cultivation. A culture period is usually 1–5 days.

Though various substances can be produced by using a suitable recombinant plasmid and host microorganism, the present method is preferably applied to the production of an amino acid by a transformant with productivity enhanced by introduction of a recombinant plasmid containing gene relating to the biosynthesis of the amino acid.

Certain embodiments of the invention are illustrated in the following examples.

EXAMPLE 1

The 3-phosphoglycerate dehydrogenase (PGDH) gene, which relates to the serine biosynthesis in *Corynebacterium glutamicum*, was incorporated into a plasmid containing the genes relating to the biosynthesis of tryptophan. The obtained recombinant plasmid was introduced into *Corynebacterium glutamicum* SA95 deficient in the PGDH gene, followed by L-tryptophan production transformant.

(1) Preparation of Chromosomal DNA of *Corynebacterium glutamicum* ATCC 31833, recombinant plasmid pCDtrp157 and vector plasmid pCG116

*Corynebacterium glutamicum* ATCC 31833 was cultured in a NB medium (20 g/l bouillon powder and 5 g/l yeast extract; pH 7.2). The resulting seed culture was inoculated into 400 ml of semi-synthetic medium SSM [20 g/l glucose, 10 g/l $(NH_4)_2SO_4$, 3 g/l Urea, 1 g/l yeast extract, 1 g/l $KH_2PO_4$, 0.4 g/l $MgCl_2.6H_2O$, 10 mg/l $FeSO_4.7H_2O$, 0.2 mg/l $MnSO_4.4-6H_2O$, 0.9 mg/l $ZnSO_4.7H_2O$, 0.4 mg/l $CuSO_4.5H_2O$, 0.09 mg/l $Na_2B_4O_7.10H_2O$, 0.04 mg/l $(NH_4)_6Mo_7O_{24}.4H_2O$, 30 µg/l biotin and 1 mg/l thiamine hydrochloride; pH 7.2] and was cultured with shaking at 30° C. The optical density (OD) at 660 nm (hereinafter the optical density is measured at 660 nm unless otherwise specified) was determined with a Tokyo Koden colorimeter, and when the OD reached 0.2, penicillin G was added to a concentration of 0.5 unit/ml. Culturing was further continued until OD reached 0.6.

The grown cells were collected from the culture and washed with TES buffer solution [0.03M tris(hydroxymethyl)aminomethane (hereinafter abbreviated as "Tris"), 0.005M disodium ethylenediaminetetraacetate (hereinafter abbreviated as EDTA) and 0.05M NaCl; pH 8.0]. The washed cells were suspended in 10 ml of a lysozyme solution (25% sucrose, 0.1M NaCl, 0.05M Tris and 0.8 mg/ml lysozyme; pH 8.0), and allowed to react at 37° C. for two hours. High molecular chromosomal DNAs were isolated from the collected cells according to the method of Saito, H. and Miura, K. [Biochim. Biophys. Acta, 72, 619 (1963)].

Construction of pCG116

Recombinant plasmid pCDtrp157 contains the 3-deoxy-D-arabino-heptulosonate-7-phosphatesynthase gene and the tryptophan biosynthetic gene cluster derived from *Corynebacterium glutamicum* (see FIG. 1) and was disclosed in Japanese Published Unexamined Patent Application No. 265892/89.

pCG116 used as a vector, is constructed by ligating a linker obtained from M13 mp18 RF DNA (Takara Shuzo Co., Ltd.) with the StuI-PstI-cleaved DNA fragment of pCG11 (Japanese Published Unexamined Patent Application No. 134500/82) autonomously replicable in *Corynebacterium glutamicum* by utilizing their blunt ends and cohesive ends. The linker is obtained by cleaving M13 mp18 RF DNA with EcoRI, repairing the cohesive end to blunt end with Klenow fragment (Takara Shuzo Co., Ltd. ), and again cleaving the DNA with PstI. Plasmid pCG116 has a molecular size of about 6.5 Kb and a single cleavage site for each of BglII, PstI, SalI, XbaI, BamHI, SmaI, KpnI and SacI, and gives a streptomycin- and/or spectinomycin-resistance phenotype (see FIG. 1).

pCDtrp157 and pCG116 were isolated individually from cultured cells of *Corynebacterium glutamicum* 31833, carrying pCDtrp157 or pCG116, according to the procedure described below.

*Corynebacterium glutamicum* ATCC 31833, carrying pCDtrp157 or pCG116 was cultured with shaking at 30° C. in 400 ml of SSM medium and treated with penicillin G in the same manner as described above, and culturing was further continued until OD reached about 0.6, The grown cells were collected, washed with TES buffer solution, and suspended in 10 ml of a lysozyme solution. The suspension was allowed to react at 37° C. for two hours. To the reaction mixture were successively added 2.4 ml of 5M NaCl, 0.6 ml of 0.5M EDTA (pH 8.5) and 4.4 ml of a solution comprising 4% sodium laurylsulfate and 0.7M NaCl, and the resulting mixture was gently stirred and placed on ice for 15 hours. The lysate thus obtained was transferred to a centrifuge tube and subjected to centrifugation at 69,400×g at 4° C. for 60 minutes to recover a supernatant. Then, polyethylene glycol (PEG) 6,000 (Nakarai Chemicals, Ltd.) was added thereto in an amount corresponding to 10% by weight. The mixture was gently stirred, and then placed on ice. After ten hours, the mixture was centrifuged at 1,500×g for ten minutes to recover pellet. Then, 5 ml of TES buffer solution was added to dissolve the pellet gradually, and 2.0 ml of 1.5 mg/ml ethidium bromide was added to the solution. Cesium chloride was added to adjust the density of the solution to 1.580.

The solution thus obtained was subjected to ultracentrifugation at 105,000×g at 18° C. for 48 hours, and a high density band at the lower part of the centrifuge tube which was detected under UV irradiation was withdrawn by puncturing the side of the centrifuge tube, using a syringe, recover the fraction containing pCDtrp157 or pCG116 plasmid DNA. The fraction was extracted five times with an equal volume of isopropanol solution [90% (V/V) isopropanol in TES buffer solution] a saturated with cesium chloride to remove ethidium bromide. Then, the solution was dialyzed against TES buffer solution.

(2) Cloning of a DNA fragment containing PGDH gene:

To 60 µl of Y-106 reaction solution (10 mM Tris, 6mM $MgCl_2$ and 100 mM NaCl; pH 7.5) containing 3 µg of pCG116 plasmid DNA isolated from *Corynebacterium glutamicum* ATCC 31833 carrying pCG116 as described above in (1) were added 6 units of restriction enzyme SalI (Takara Shuzo Co., Ltd.; unless otherwise specified, restriction enzymes hereinafter used are products of Takara Shuzo Co., Ltd.), and the mixture was allowed to react at 37° C. for 60 minutes. Separately, 6 units of restriction enzymes SalI were added to 140 µl of Y-100 reaction solution containing 3 µg of the chromosomal DNA of *Corynebacterium glutamicum* ATCC 31833 obtained as described above in (1), and the mixture was allowed to react at 37° C. for 60 minutes. The both reactions were stopped by heating at 65° C. for ten minutes.

To the both reaction mixtures thus obtained were mixed, and 40 µl of a buffer solution for T4 ligase at a 10-fold concentration (660 mM Tris, 66 mM MgCl$_2$ and 100 mM dithiothreitol; pH 7.6 ), 40 µl of 5 mM ATP, 300 units of T4 ligase (Takara Shuzo Co., Ltd. ) and 120 µl of water were added thereto. Then, the mixture was allowed to react at 12° C. for 16 hours.

The reaction mixture was used for transformation of *Corynebacterium glutamicum* RS57 (a serine-requiring mutant deficient in PGDH gene derived from *Corynebacterium glutamicum* ATCC 31833.) A seed culture of this strain (4 ml) was inoculated into 40 ml of SSM medium containing 100 µg/ml serine, and cultured with shaking at 30° C. When OD reached 0.2, the culture was treated with penicillin G in the same manner as above in (1), and culturing was further continued until OD reached 0.6. The grown cells were collected and suspended to a concentration of about 10$^9$ cells per milliliter in 10 ml of RCGP medium [5 g/l glucose, 5 g/l Casamino acid, 2.5 g/l yeast extract, 3.5 g/l K$_2$HPO$_4$, 1.5 g/l KH$_2$PO$_4$, 0.41 g/l MgCl$_2$. 6H$_2$O, 10 mg/l FeSO$_4$.7H$_2$O, 2 mg/l MnSO$_4$.4-6H$_2$O, 0.9 mg/l ZnSO$_4$. 7H$_2$O, 0.04 mg/l (NH$_4$)$_6$Mo$_7$O$_{24}$.4H$_2$O, 30 µg/l biotin, 2 mg/l thiamine hydrochloride, 135 g/l disodium succinate and 30 g/l polyvinyl pyrrolidone (M.W.: 10,000); pH 7.6] containing 1 mg/ml lysozyme. The suspension was transferred to an L-type test tube and gently shaken at 30° C. for 16 hours to prepare protoplasts.

Then, 0.5 ml of the protoplast suspension thus was transferred to a small test tube and centrifuged at 2,500×g for five minutes to separate the protoplasts. The protoplasts were suspended in 1 ml of TSMC buffer solution (10 mM MgCl$_2$, 30 mM CaCl$_2$, 50 mM Tris, 400 mM sucrose, pH 7.5) and the suspension was centrifuged for washing. The washed protoplasts were resuspended in 0.1 ml of TSMC buffer solution. Then, 100 µl of a 1:1 mixture of TSMC buffer solution at a two-fold concentration and the ligation reaction mixture obtained above was added to the protoplast suspension. 0.8 ml of TSMC buffer solution containing 20%. PEG 6,000 was then added to the resulting mixture. After three minutes, 2 ml of a RCGP medium (pH 7.2) was added thereto and the resulting mixture was centrifuged at 2,500×g for 5 minutes to remove a supernatant. The precipitated protoplasms were suspended in 1 ml of RCGP medium. 0.2 ml of the suspension was spread on RCGP agar medium (prepared by adding 1.4% agar to RCGP medium) containing 400 µg/ml of spectinomycin and cultured at 30° C. for 7 days. After culturing, the colonies grown on RCGP agar medium were scraped up, and washed twice with physiological saline solution by centrifugation. The washed cells were suspended in 1 ml of physiological saline solution. The suspension was spread on minimal agar medium M1 [10 g/l glucose, 1 g/l (NH$_4$)H$_2$PO$_4$, 0.2 g/l KCl, 0.2 g/l MgSO$_4$.7H$_2$O, 10 mg/l FeSO$_4$.7H$_2$O, 0.2 mg/l MnSO$_4$.4-6H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$.4H$_2$O, 50 µg/l biotin, 2.5 mg/l p-aminobenzoic acid, 1 mg/l thiamine hydrochloride and 16 g/l agar; pH 7.2] containing 100 µg/ml of spectinomycin and cultured at 30° C. for 3 days to select for transformants which are resistant to spectinomycin and not requiring serine. Plasmid DNA was isolated from the selected transformants in the same manner as described above in (1). The plasmid DNA was digested with various restriction enzymes and the restriction fragments were analyzed by agarose gel electrophoresis, the plasmid named pCser571 was found to contain a 2.7 kb SalI-cleaved DNA fragment at the-SalI site of pCG116 (see FIG. 1).

PGDH activities of *Corynebacterium glutamicum* ATCC 31833 and the transformant carrying pCser571 were determined according to the method described by E. Sugimoto and L. I. Pizer [J. Biol. Chem., 243 2081(1968)]. It was demonstrated that PGDH activity of the transformant carrying pCser571 is about 13 times high as that of ATCC 31833 strain. This indicates that the cloned DNA fragment contains the PGDH gene.

(3) Ligation of a DNA fragment containing the PGDH gene to pCDtrp157

To 100 µl of Y-100 reaction solution containing 3 µg of pCser571 plasmid DNA was added 6 units of BamHI, and the mixture was allowed to react at 37° C. for 60 minutes. After digestion, the mixture was electrophoresed on agarose gel and the 1.4 kb DNA fragment was cut out of the gel. Separately, 6 units of BamHI was added to 100 µl of reaction solution Y-100 containing 3 µg of pCDtrp157 plasmid DNA, and the mixture was allowed to react at 37° C. for 60 minutes. The reaction was stopped by heating at 65° C. for 10 minutes. Both reaction mixture thus obtained were mixed, and twice the volume of ethanol was added to the mixture. After precipitation, the DNA was recovered and suspended in 200 µl of water. To 200 µl of the DNA suspension were added 40 µl of buffer solution for T4 ligase at a 10-fold concentration, 40 µl of 5 mM ATP, 300 units of T4 ligase and 120 µl of water and the mixture was allowed to react at 12° C. for 16 hours. The reaction mixture was used for transformation of RS57 in the same manner as described in (2). The transformation mixture was spread on RCGP agar medium containing 400 µg/ml of spectinomycin and the plate-was cultured. After culturing, the spectinomycin-resistant colonies grown on RCGP agar medium were scraped up, and washed twice with physiological saline solution by centrifugation. The washed cells were suspended in 1 ml of physiological saline solution. The cell-suspension was spread on minimal agar medium L1 containing 100 µg/ml of spectinomycin, and cultured at 30° C. for 3 days to select for transformants resistant to spectinomycin and not requiring serine. Plasmid DNA was isolated from these transformants in the same manner as described in (1). The plasmid DNA was digested with various restriction enzymes and the restriction fragments were analyzed by agarose gel electrophoresis. The plasmids obtained from one of the transformants and named pDTS9901 was found to contain a 1.4 kb BamHI-cleaved DNA fragment at the BamHI site of pCDtrp157 (see FIG. 1). The plasmid pDTS9901 obtained as described above was used for transformation of *Corynebacterium glutamicum* ATCC 21854, a phenylalanine-and tyrosine-requiring strain which is derived from *Corynebacterium glutamicum* ATCC 13032, in the same manner as described above. *Corynebacterium glutamicum* ATCC 21854 carrying pDTS9901 was deposited in the Fermentation Research Institute (FRI), Agency of Industrial Science and Technology, Japan under Budapest Treaty on Jun. 2, 1989 as *Corynebacterium glutamicum* K82, and was assigned the accession number FERM BP-2444.

(4) Production of L-tryptophan by Transformant Carrying pCDtrp157 or pDTS9901 and Stability of Plasmid Seed culture (4 ml) of each of *Corynebacterium glutamicum* ATCC 21854 and *Corynebacterium glutamicum* SA95 was inoculated into 40 ml of SSM medium containing 100 µg/ml of each of phenylalanine, tyrosine, and serine, and cultured with shaking at 30° C.

*Corynebacterium glutamicum* SA95 is a serine-requiring strain lacking the PGDH gene and derived from *Corynebacterium glutamicum* ATCC 21854, was deposited with FRI, Agency of Industrial Science and Technology, Japan under Budapest Treaty on Sep. 21, 1990, and was assigned the accession number FERM BP-3108.

When OD reached 0.2, treatment with penicillin G was carried out in the same manner as described in (1), and culturing was further continued until OD reached 0.6. The grown cells were collected and treated with lysozyme in the same manner as described in (2). The resulting protoplasts thus obtained were transformed in the same manner as described in (2) with pCDtrp157 or pDTS9901. Plasmid DNAs were isolated in the same manner as described in (1) from spectinomycin-resistant transformants thus obtained. From restriction cleavage analysis of the plasmids, it was confirmed that these transformants carry pCDtrp157 or pDTS9901. L-tryptophan production test of the transformants was carried out as described below. Each transformant was cultured with shaking in 3 ml of a S1 medium [20 g/l glucose, 15 g/l polypeptone, 15 g/l yeast extract, 2.5 g/l NaCl, 1 g/l Urea, 200 mg/l L-tyrosine, 200 mg/l L-phenylalanine; pH 7.2] at 30° C. for 24 hours. 0.5 ml of the culture was inoculated into 5 ml of a production medium P1 [60 g/l glucose, 1 g/l $KH_2PO_4$, 1 g/l $K_2HPO_4$, 1 g/l $MgSO_4.7H_2O$, 20 g/l $(NH_4)_2SO_4$, 10 g/l corn steep liquor, 10 mg/l $MnSO_4$, 30 µg/l biotin, 20 g/l $CaCO_3$; pH 7.2] in a large test tube and cultured with shaking at 30° C. for 72 hours. After culturing, the culture was filtered and L-tryptophan in the filtrate was quantitated by high performance liquid chromatography according to the o-phthalaldehyde/2-mercaptoethanol-post column derivatization method.

Stability of plasmids in the host cell was tested by a growth of colonies on NB agar medium containing 100 µg/ml of spectinomycin:

The grown culture was diluted and the dilution was spread on NB agar medium. Colonies grown on the NB agar medium were transferred to a NB agar medium containing 100 µg/ml of spectinomycin.

*Corynebacterium glutamicum* SA95 carrying pDTS9901 was found to stably maintain the plasmid in the cell (see Table 1).

TABLE 1

| Strain | L-tryptphan (mg/ml) | Plasmid stability (%) |
| --- | --- | --- |
| ATCC 21854 (pCDtrp157) | 4.3 | 68 |
| ATCC 21854 (pDTS9901) | 4.6 | 62 |
| SA95 (FERM BP-3108)/pDTS9901 | 5.4 | 100 |

EXAMPLE 2

The PGDH gene, which relates to the serine biosynthesis in *Corynebacterium glutamicum*, was incorporated into a plasmid containing the threonine biosynthesis genes. The obtained recombinant plasmid was introduced into *Corynebacterium glutamicum* SA24 deficient in the PGDH gene, followed by L-threonine production test on the transformant.

Figure 2:
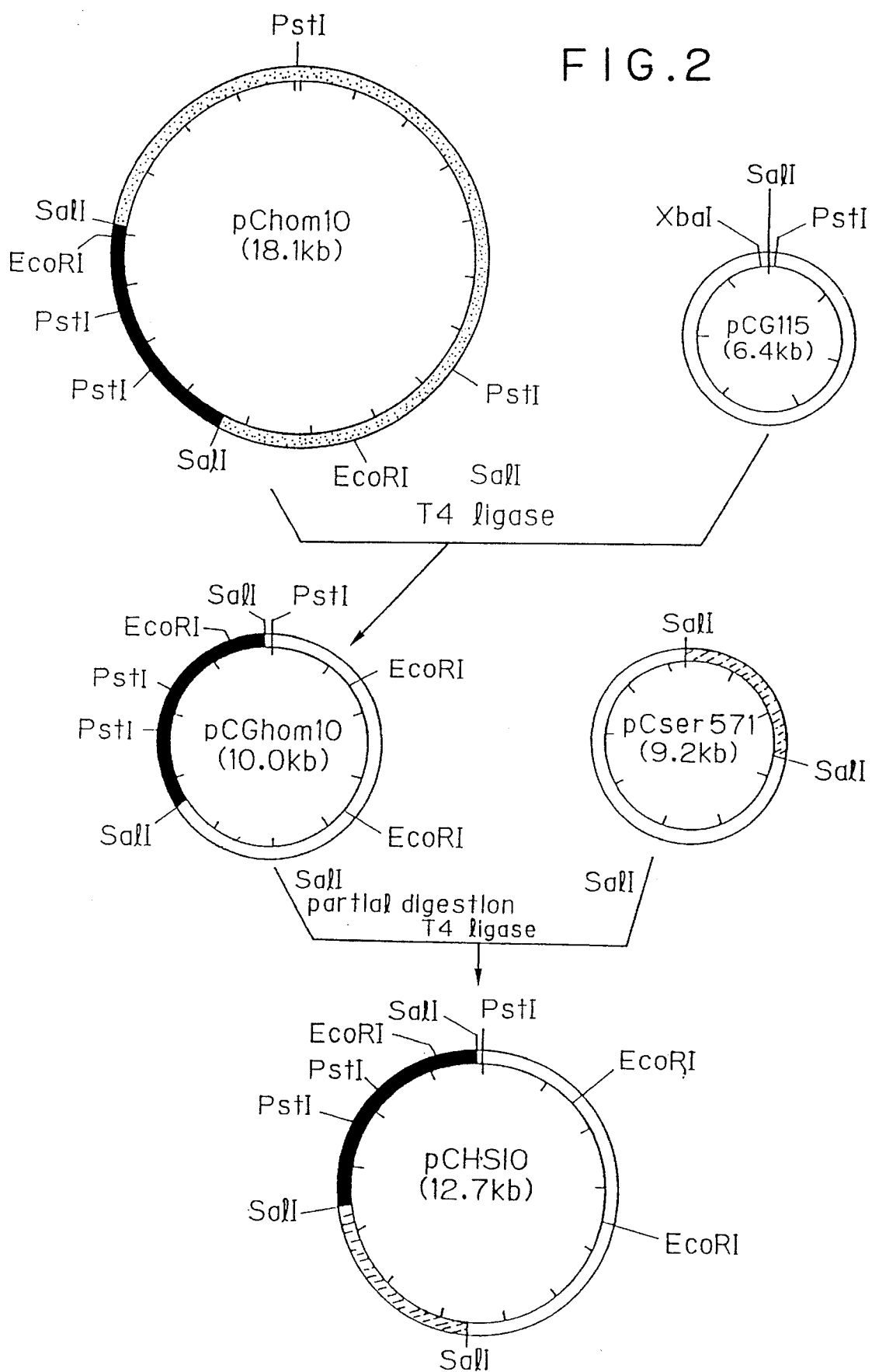
FIG. 2 illustrates the restriction enzyme cleavage map for pCHS10 and the steps for constructing it. The homoserine dehydrogenase (HD) gene and the homoserine kinase (HK) gene are located on the chromosomal DNA-fragment indicated by a thick solid lane, and the PGDH gene is located on the fragment indicated by broken lines.

(1) Preparation of Recombinant Plasmid pChom10 and Vector pCG115 pChom10 was constructed by inserting a 3.6 kb DNA fragment- containing the homoserine dehydrogenase (HD) gene and homoserine kinase (HK) genes of *Corynebacterium glutamicum* described in Japanese Published Unexamined Patent Application No. 91193/87 into the SalI site of vector pCE54 described in Japanese Published Unexamined Patent Application No. 105999/83 (see FIG. 2).

pCG115 used as a vector, is constructed by ligating a linker obtained from M13 mp18 RF DNA with the BglII-PstI-cleaved DNA fragment of pCG11 by utilizing their same cohesive ends. The linker is obtained by cleaving M13 mp18 RF DNA with BamHI and PstI.

Plasmid pCG115 has molecular size of about 6.4 kb and a single cleavage for each of site XbaI, SalI and PstI, and gives a streptomycine- and/or spectinomycin-resistance phenotype (see FIG. 2).

pChom10 and pCG115 were isolated individually from cultured cells of *Corynebacterium glutamicum* ATCC 31833 in the same manner as described in Example 1 (1).

(2) Ligation of a DNA fragment Containing the HD and HK genes to pCG115

To 200 µl of Y-100 reaction solution containing individually 3 µg of pChom10 plasmid DNA and pCG115 plasmid DNA was added 6 units of BamHI. The reaction mixture was allowed to react at 37° C. for 60 minutes and the reaction was stopped by heating the reaction mixture at 65° C. for 10 minutes. To 200 µl of the DNA suspension were added buffer solution for T4 ligase at 10-fold concentration, 40 µl of 5 mM ATP, 300 units of T4 ligase and 120 µl of water and the mixture was allowed to react at 12° C. for 16 hours. The reaction mixture was used for transformation of *Corynebacterium glutamicum* K54 (FERM P-8258), a threonine-requiring mutant deficient in HK gene derived from *Corynebacterium glutamicum* ATCC 31833, in the same manner as described in Example 1 (2). The transformation mixture was spread on RCGP agar medium containing 400 µg/ml of spectinomycin. The spectinomycin-resistant colonies grown on RCGP agar medium were scraped up, and washed twice with physiological saline solution by centrifugation. The washed cells were suspended in 1 ml of physiological saline solution. The cell suspension was spread on minimal agar medium M1 containing 100 µg/ml of spectinomycin and cultured at 30° C. for 3 days to select for transformants resistant to spectinomycin and not requiring threonine. Plasmid DNA was isolated from these transformants in the same manner as described in Example 1 (1). The plasmid DNA was digested with various restriction enzymes and the restriction fragments were analyzed by agarose gel electrophoresis. The plasmid obtained from one of the transformants and named pCG115, was found to contain a 3.6 kb SalI-cleaved DNA fragment at the SalI site of pCG115 (see FIG. 2).

(3) Ligation of a DNA fragment Containing the PGDH Gene pCGhom10.

To 100 µl of Y-100 reaction solution containing 3 µg of pCser571 plasmid DNA was added 6 units of SalI. The reaction mixture was allowed to reach at 37° C. for 60 minutes. After digestion, the mixture was electrophoresed on agarose gel and the 2.7 kb DNA fragment was cut out of the gel. Separately 0.5 unit of SalI was added to 100 µl of Y-100 reaction solution containing 3 ∥g of pCGhom10 plasmid DNA. The reaction mixture was allowed to react at 37° C. for 10 minutes. After digestion, the mixture was electrophoresed on agarose gel, and the DNA fragment of 10.0 kb was cut out of the gel. Both reaction mixture thus obtained were mixed and twice the volume of ethanol was added thereto. After precipitation, the DNA was recovered and suspended in 200 µl of water. To the DNA suspension were added 40 µl of buffer solution for. T4 ligase at a 10-fold concentration, 40 µl of 5 mM ATP, 300 units of T4 ligase, 12° C. of water and the mixture was allowed to react at 12° C. for 16 hours. The reaction mixture was used for transformation of *Corynebacterium glutamicum* RS 57 in the same manner as described in Example 1 (1). Then, transformants resistant to spectinomycin and not requiring threonine were selected. Plasmid DNA was isolated from these transformants in the same manner as described in Example 1 (1). The plasmid DNA was digested with various restriction enzymes and the restriction fragments were analyzed by agarose gel electrophoresis. The plasmid obtained from one of the transformants and named pCHS10, was found to contain a 2.7 kb SalI-cleaved DNA fragment at one of two SalI sites of pCGhom10 (see FIG. 2).

(4) L-threonine Production by Transformant Carrying pCGhom10 or pCHS10 and Stability of Plasmids in Host Cells

*Corynebacterium glutamicum* ATCC 13032 and *Corynebacterium glutamicum* SA 24, a serine-requiring mutant deficient in PGDH gene derived from *Corynebacterium glutamicum* ATCC 13032, were transformed with pCGhom10 or pCHS10 in the same manner as described in Example 1(2). Then the plasmid DNA was isolated from the resulting spectinomycin resistant transformants. By restriction cleavage analysis, the transformants were found to contain pCGhom10 or pCHS10.

The transformants were tested for L-threonine production as described below. Each transformant was cultured with shaking in 3 ml of NB medium at 30° C. for 24 hours. 0.5 ml of the culture was inoculated into 5 ml of production medium T [200 g/l blackstrap molasses, 0.3 g/l $KH_2PO_4$, 0.4 g/l $MgSO_4.7H_2O$, 20 g/l $(NH_4)_2SO_4$, 10 mg/l $FeSO_4.7H_2O$, 10 mg/l $MnSO_4.4-6H_2O$, 8 g/l corn steep liquor, 200 µg/l of thiamine hydrochloride, 200 µg/l biotin, 40 g/l $CaCO_3$; pH 7.2] in a large test tube and cultured with shaking at 30° C. for 72 hours. After culturing, the culture was filtered and L-threonine in the filtrate was quantitated by high performance liquid chromatography according to the o-phthalaldehyde/2-mercaptoethanol-post column derivatization method.

Stability of plasmids in the host cell was tested in the same manner as described in Example 1 (4).

*Corynebacterium glutamicum* SA 24 carrying pCHS10 was found to stably maintain the plasmid in the cell (see Table 2).

TABLE 2

| Strain | L-threonine (mg/ml) | Plasmid stability (%) |
|---|---|---|
| ATCC 13032/pCGhom10 | 1.9 | 85 |
| ATCC 13032/pCHS10 | 1.9 | 81 |
| SA 23/pCHS10 | 2.2 | 100 |

What is claimed is:

1. A process for maintaining a recombinant DNA stably in a microorganism host belonging to the genus Corynebacterium or Brevibacterium, which comprises transforming a serine auxotrophic microorganism host belonging to the genus Corynebacterium or Brevibacterium by introducing into said host a recombinant plasmid containing a gene which complements the serine auxotrophy of the host.

2. The process according to claim 1, wherein said gene encodes an enzyme in the serine biosynthetic pathway and said enzyme is selected from the group consisting of 3-phosphoglycerate dehydrogenase, phosphoserine aminotransferase, and phosphoserine phosphatase.

3. The process according to claim 1, wherein said recombinant plasmid further contains a second gene which encodes an enzyme in the biosynthetic pathway of an amino acid.

* * * * *